United States Patent [19]

Manimaran

[11] Patent Number: 5,498,800
[45] Date of Patent: Mar. 12, 1996

[54] ULTRASONIC PROCESS

[75] Inventor: Thanikavelu Manimaran, Baton Rouge, La.

[73] Assignee: Albemarle Corporation, Richmond, Va.

[21] Appl. No.: 370,057

[22] Filed: Jan. 9, 1995

[51] Int. Cl.$^6$ ............................. C07C 45/43; C07C 1/00
[52] U.S. Cl. ..................... 568/437; 568/426; 585/612; 585/638; 585/657
[58] Field of Search ..................... 568/426, 437, 568/488, 490; 568/488, 490; 585/612, 638, 657

[56] References Cited

U.S. PATENT DOCUMENTS

| | | | |
|---|---|---|---|
| 4,225,694 | 9/1980 | Dalton, Jr. et al. | 568/437 |
| 4,229,379 | 10/1980 | Brühne et al. | 568/437 |
| 4,328,374 | 5/1982 | Yoshinaka | 568/436 |
| 4,450,298 | 5/1984 | Kondow | 568/437 |
| 4,474,993 | 10/1984 | Hag et al. | 568/437 |
| 5,347,054 | 9/1994 | Billeb et al. | 568/437 |
| 5,382,694 | 1/1995 | Billeb et al. | 568/437 |

FOREIGN PATENT DOCUMENTS

| | | | |
|---|---|---|---|
| 0599214 | 6/1994 | European Pat. Off. | 568/437 |
| 0599241 | 6/1994 | European Pat. Off. | 568/437 |

*Primary Examiner*—Werren B. Lone
*Attorney, Agent, or Firm*—Philip M. Pippenger

[57] ABSTRACT

A process is disclosed for obtaining a compound of the formula $$Ar-Z \qquad \qquad II$$

where Ar, $R_1$ and $R_2$ are defined in the specification and Z is $-C(R_3)=CH_2$ or $-CH(R_3)CHO$ where $R_3$ is defined in the specification. The process utilizes a heterogeneous mixture of the compound of formula I and an alkali or alkaline earth metal in dimethylformamide. The mixture is subjected to ultrasonic vibrations for a time and at a temperature sufficient to produce a compound of formula II:

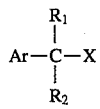

where Ar, $R_1$, and $R_2$ are defined above and X is the halo group.

12 Claims, No Drawings

ULTRASONIC PROCESS

FIELD OF INVENTION

A process is disclosed for the preparation of aryl-substituted aliphatic olefins or aldehydes by ultrasonic vibration. Specifically, a benzylic halide is reacted with a metal in dimethylformamide under ultrasonic conditions to produce the corresponding benzylic olefin or aidehyde.

BACKGROUND OF INVENTION

While a great deal of research has provided numerous examples where ultrasound (sound waves whose frequencies lie within the range of 20 to 10,000 kHz) has been used to activate metal surfaces, the literature does provide a limited number of examples where inorganic bases can be used under heterogeneous conditions in organic reactions.

Shibata et al. have described the cyanomethylation of a variety of chalcones by the Michael addition of the radical anion derived from acetonitrile. Sonolysis for about fifteen minutes in the presence of potassium peroxide produced the desired nitrile. See Shibata et al., *Chem. Lett.*, 519 (1987). Other sonochemical methods permit the use of cyanides of various metals to lengthen the carbon chain by one unit under extremely simple conditions. Acyl cyanide, for example, is readily prepared at low temperatures using potassium cyanide under ultrasonic conditions. Conventional methods require copper, silver or thallium salts. Ando et al., *Synthesis*, 637 (1983).

There remains a need to develop a method for preparing substantially pure, simple olefins or aldehydes under mild conditions in a single step with few competing reactions. Under drastic conditions, these products tend to undergo further reactions resulting in impure products.

OBJECTS OF THE INVENTION

It is an object of the present invention to provide a process for obtaining a substantially pure aryl-substituted aliphatic olefins or aldehydes in a single step starting with a halogen precursor.

It is a further object of the present invention to obtain such a substantially pure compound by treating solution of said halogen precursor and an alkaline earth or alkali metal with ultrasonic frequencies.

PREFERRED EMBODIMENTS OF THE INVENTION

In the present specification, "alkyl" means straight or branched chain alkyl having 1 to 20 carbon atoms and includes, for example, methyl, ethyl, propyl, isopropyl, butyl, isobutyl, secondary butyl, tertiary butyl, pentyl, isopentyl, neopentyl, hexyl, heptyl, octyl, 2-ethylhexyl, 1,1,3,3-tetramethylbutyl, nonyl, decyl, dodecyl, tetradecyl, hexadecyl, octadecyl and eicosyl;

"cycloalkyl" means cyclic alkyl having 3 to 7 carbon atoms and includes cyclopropyl, cyclobutyl, cyclopentyl, cyclohexyl and cycloheptyl;

"alkyl-substituted cycloalkyl" means the above cycloalkyl group substituted by one or more alkyl groups;

"substituted phenyl" or "substituted naphthyl" means phenyl or naphthyl substituted by at least one substituent selected from the group consisting of halo (chlorine, bromine, fluorine or iodine), amino, nitro, hydroxy, alkyl, alkoxy which means straight or branched chain alkoxy having 1 to 10 carbon atoms, and includes, for example, methoxy, ethoxy, propoxy, isopropoxy, butoxy, isobutoxy, secondary butoxy, tertiary butoxy, pentyloxy, isopentyloxy, hexyloxy, heptyloxy, octyloxy, nonyloxy an decyloxy, haloalkyl which means straight or branched alkyl having 1 to 8 carbon atoms which is substituted by at least one halo (or halogen), and includes, for example, chloromethyl, bromomethyl, fiuoromethyl, iodomethyl, 2-chloroethyl, 2-bromoethyl, 2-fiuoroethyl, 3-chloropropyl, 3-bromopropyl, 3-fluoropropyl, 4-chlorobutyl, 4-fluorobutyl, dichloromethyl, dibromomethyl, difiuoromethyl, diiodomethyl, 2,2-dichloroethyl, 2,2-dibromoethyl, 2,2-difluoroethyl, 3,3-dichloropropyl, 3,3-difluoropropyl, 4,4-dichlorobutyl, 4,4-difluorobutyl, trichloromethyl, trifluoromethyl, 2,2,2-trifluoroethyl, 2,3,3-trifluoropropyl, 1,1,2,2-tetrafluoroethyl and 2,2,3,3-tetrafluoropropyl;

By the term "alkylthio" means straight or branched chain hydrocarbon thioether groups of six or less carbon atoms, including methylthio, ethylthio, propylthio, 2-propylthio, 2-butylthio, pentylthio, 3-hexylthio, and the like.

The term "thioether" as used herein describes ether groups conventionally employed in the art, preferably those derived from normal chain, branched chain, cyclic and aromatic hydrocarbons. The term "hydrocarbon" defines both substituted and unsubstituted hydrocarbons. These hydrocarbons are optionally substituted with groups such as hydroxy, alkoxy, alkylthio, halo, and the like. Preferably the hydrocarbons contain from 1 to 12 carbon atoms. Typical thioethers thus include alkylthio, dihaloalkylthio, i.e., alkoxyalkylthio, i.e., alkoxymethylthio, alkylthioalkylthio, i.e., alkylthiomethylthio, and the like.

"alkanoyl" means alkanoyl having 2 to 18 carbon atoms and includes, for example, acetyl, propionyl, butyryl, isobutyryl, pivaloyl, valeryl, hexanoyl, octanoyl, lauroyl and stearoyl;

"substituted benzoyl" or "substituted naphthanoyl" means benzoyl or naphthanoyl which is substituted by at least one substituent selected from the group consisting of halogen, amino, nitro, hydroxy, alkyl, alkoxy and haloalkyl on the benzene ring;

"heteroaryl" means 5 to 10 membered mono or fused-heteroaromatic ring which has at least one heteroatom selected from the group consisting of nitrogen, oxygen and sulfur, and includes, for example, 2-furyl, 3-furyl, 2-thienyl, 3-thienyl, 2-pyridyl, 3-pyridyl, 4-pyridyl, pyrazolyl, imidazolyl, pyrimidinyl, pyridazinyl, pyrazinyl, benzimidazolyl, quinolyl, oxazolyl, thiazolyl and indo;

"substituted heteroaryl" means 5 to 10 membered mono- or fused-heteroaromatic ring which has at least one heteroatom selected from the group consisting of nitrogen, oxygen and sulfur and which is substituted by at least one substituent selected from the group consisting of halogen, amino, nitro, hydroxy, alkyl, alkoxy and haloalkyl on the above-mentioned heteroaromatic nucleus;

"heteroarylcarbonyl" means that the heteroaryl moiety is 5 to 10 membered mono- or fused-heteroaromatic ring having at least one heteroatom selected from the group consisting of nitrogen, oxygen and sulfur as mentioned above, and includes, for example, furoyl, thienoyl, nicotinoyl, isonicotinoyl, pyrazolylcarbonyl, imidazolylcarbonyl, pyrimidinylcarbonyl and benzimidazolylcarbonyl;

"substituted heteroarylcarbonyl" means the above-mentioned heteroarylcarbonyl which is substituted by at least one substituent selected from the group consisting of halogen, amino, nitro, hydroxy, alkoxy and haloalkyl on the heteroaryl nucleus; and "Alkoxycarbonyl" may be represented, for example, by the formula C(O)O-alkyl. In this formula, "alkyl" represents a straight-chain or branched hydrocarbon radical having 1 to 12 carbon atoms. Lower alkoxycarbonyl having 1 to about 4 carbon atoms in the alkyl part is preferred. Alkoxycarbonyl, having 1 to 4 carbon atoms in the alkyl part, is particularly preferred. Examples which may be mentioned are the following alkoxycarbonyl radicals: methoxycarbonyl, ethoxycarbonyl, propoxycarbonyl, isopropoxycarbonyl, butoxycarbonyl or isobutoxycarbonyl.

"Aryloxycarbonyl" may be represented, for example, by the formula —C(O)O-aryl. In this formula, "aryl" represents an aromatic radical having 6 to 12 carbon atoms. Examples of such aromatic radicals include: phenoxycarbonyl and naphthyloxycarbonyl.

The objective of the present invention is achieved by dissolving an aryl-substituted aliphatic halide in an inert solvent or a mixture of inert solvents. The halide has the following formula:

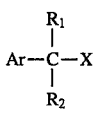

I where X is halogen; $R_1$ and $R_2$ are hydrogen, alkyl, cycloalkyl, alkyl-substituted cycloalkyl phenyl, substituted phenyl, naphthyl, substituted naphthyl, alkoxy, alkylthio, heteroaryl either substituted or unsubstituted alkonoyl, benzoyl or naphthanoyl either substituted or unsubstituted, alkoxycarbonyl, aryloxycarbonyl, trifluoromethyl or halo; and Ar is phenyl, substituted phenyl, naphthyl or substituted naphthyl.

Preferred compounds of Formula I are those of the formula:

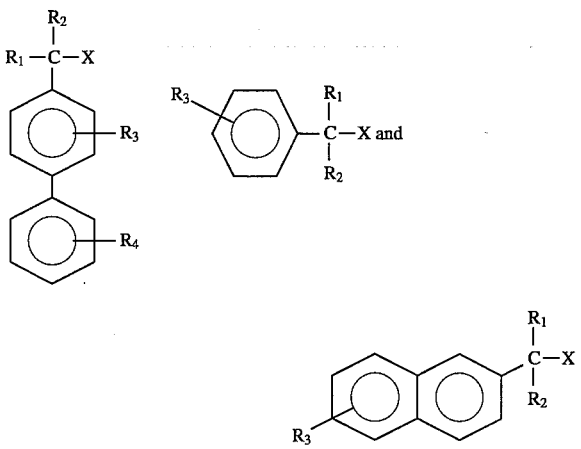

where X, $R_1$, and $R_2$ are as previously defined and $R_3$ and $R_4$ are $C_1$ to $C_4$ linear or branched alkyl, $C_1$ to $C_4$ linear or branched alkoxy or halo.

The process of the present invention is particularly applicable to 1-( 4-isobutylphenyl)-1-chloroethane.

The process of the present invention is carried out by treating a compound of formula I with ultrasound in the presence of an alkali or alkaline earth metal. This process is sometimes called sonication. Typically, the sonication is conducted in a heterogeneous anhydrous medium comprised of a liquid medium that is the compound of formula I admixed with the solid metal. However, in some cases the compounds of formula I are not mobile liquids but are very viscous liquids. In such cases, it is advantageous to dissolve the compounds for formula I in an inert (anhydrous) solvent, such as a polar solvent. Acceptable solvents are those including dimethylsulfoxide, dimethylformamide, tetrahydrofuran, methylethylketone and ethyl alcohol.

Of course, it should be understood that this sonochemical reaction must be carried out in a heterogeneous medium. Thus, should the compounds of formula I be solid, then either the metal should be a liquid or dissolved in an inert solvent that does not dissolve the compound of formula I or the compound of formula I should be dissolved in an inert solvent that does not dissolve the metal.

The alkali or alkaline earth metals that are of use in the process of the present invention are those that, under ultrasonic conditions, provide the metal anion that attacks the halogen group in the compounds of formula I. The metals of Group IA or IIA are preferred, e.g., potassium, sodium, lithium, or magnesium. Particularly preferred is lithium in the reaction where Z in the compound of formula II contains the group —CHO, i.e., the aldehyde group. Where Z is the group =, a particularly preferred metal is sodium.

The process of the present invention utilizing the heterogeneous mixture disclosed above provides compounds of the following Formula II Ar-Z    II where Ar is as previously defined and Z is the group $C(R_3)=CH_2$ or the group —$CH(R_3)CHO$ where $R_3$ is as previously defined.

The present invention embraces any of the racemates and individual optical isomers thereof of the compounds of formula (II) having an achiral carbon atom.

The process of the present invention is accomplished by sonication of the reaction mixture of alkali or alkaline earth metal and halo compound of formula I for a time and at a temperature sufficient to produce the compounds of formula II. Those skilled in the art of sonication chemistry readily appreciate these parameters of the reaction. For example, temperatures from about room temperature (25° C.) to about 100° C. are useful in carrying out this reaction. A reaction time from as little as about 15 minutes up to about 24 hours can be used. Preferably the reaction is carried out at about 30° C. to 50° C. for 5 to 15 hours. The presence of a phase transfer agent has, in some cases, been found beneficial to the sonication process, e.g., benzyl triethylammonium bromide.

The product of the reaction is easily separated from the reaction mass by any suitable conventional method, e.g., vacuum distillation, solvent extraction, recrystallization, etc.

The following examples are included herewith for illustrative purposes only. They are not to be regarded as a limitation to the claims setting forth the process of this invention.

EXPERIMENTAL

Dehydrohalogenation by Sonication

EXAMPLE 1

A flat bottomed vial was charged with a mixture of 1-chloro-1-(4-isobutylphenyl)ethane (500 mg; 2.54 mmol), 250 mg (11 mmol) of sodium spheres in 5 mL of dry dimethylformamide. The vial was immersed in an ultrasound cleaner filled with water, and sonicated at room temperature for 2 hours. The reaction mixture was carefully treated with 30 mL of water and extracted with ether (3×30 mL). The ether extract was washed with water (3 ×15 mL) and dried over anhydrous $MgSO_4$. It was filtered and stripped off the solvent to obtain 382 mg (94% yield) of pure 4-isobutylstyrene.

EXAMPLE 2

A vial was charged with a mixture of 1-chloro-1-(4-isobutylphenyl)ethane (600 mg; 3 mmol), 70 mg of magnesium turnings (3 mmol), 300 mg (4 mmol) of dimethylformamide and 4 mL of dry THF solvent. The mixture was sonicated at room temperature overnight. By gas chromatographic analysis, the mixture was found to contain 83% of the starting chloride and 6% of 4-isobutylstyrene.

Formylation by Sonication

EXAMPLE 3

A flask was charged with 400 mg (2 mmol) of 1-chloro-1-(4-isobutylphenyl)ethane, 200 mg (2.7 mmol) of dry dimethylformamide, 50 mg (7 mmol) of lithium powder and 5 mL of toluene under an argon atmosphere. The mixture was sonicated at room temperature for 5 hours. The mixture was then carefully treated with 10 mL of water and extracted with ether. By gas chromatographic analysis, the ether phase was found to contain the starting chloride and 1-(4-isobutylphenyl)propionaldehyde as the product −45% yield at 76% conversion.

I claim:

1. A process for preparing a compound of the following formula:

Ar-Z   II where Ar is phenyl, naphthyl, substituted phenyl or substituted naphthyl; Z is the group $C(R_3)=CH_2$ or $CH(R_3)CHO$ where $R_3$ is hydrogen or alkyl which comprises treating an anhydrous solution of an aliphatic halide of the following formula:

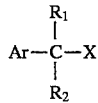   I where $R_1$ and $R_2$ are hydrogen, alkyl, cycloalkyl, alkyl-substituted cycloalkyl, phenyl or naphthyl either substituted or unsubstituted, alkoxy, alkylthio, heteroaryl either substituted or unsubstituted, alkanoyl, benzoyl or naphthanoyl either substituted or unsubstituted, heteroarylcarbonyl either substituted or unsubstituted, alkoxycarbonyl, aryloxycarbonyl, trifluoromethyl or halo; X is halo with an alkaline earth or alkali metal at an ultrasonic frequency for a time and at a temperature sufficient to produce said compound.

2. The process according to claim 1 where said solution is formed from a polar organic solvent.

3. The process according to claim 2 wherein said polar organic solvent is dimethylformamide.

4. The process according to claim 1 wherein Ar is substituted phenyl or substituted naphthyl and X is chloro or bromo.

5. The process according to claim 3 wherein Ar is phenyl substituted with isobutyl.

6. The process according to claim 1 wherein X is chloro.

7. The process according to claim 1 wherein said aliphatic halide is dissolved in an anhydrous polar solvent.

8. The process according to claim 6 wherein said metal is an alkali metal.

9. The process according to claim 7 wherein said metal is sodium and Z is the group $C(R_3)=CH_2$.

10. The process according to claim 9 wherein $R_3$ is hydrogen.

11. The process according to claim 7, wherein said metal is lithium and Z is the group $CH(R_3)CHO$.

12. The process according to claim 11 wherein $R_3$ is methyl.

* * * * *